United States Patent
Baba et al.

(10) Patent No.: US 9,247,923 B2
(45) Date of Patent: Feb. 2, 2016

(54) RECEIVED DATA PROCESSING APPARATUS OF PHOTOACOUSTIC TOMOGRAPHY

(75) Inventors: Yoshitaka Baba, Tokyo (JP); Haruo Yoda, Nishitama-gun (JP); Kazuhiko Fukutani, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 278 days.

(21) Appl. No.: 13/055,632

(22) PCT Filed: Sep. 3, 2009

(86) PCT No.: PCT/JP2009/065773
§ 371 (c)(1),
(2), (4) Date: Jan. 24, 2011

(87) PCT Pub. No.: WO2010/027095
PCT Pub. Date: Mar. 11, 2010

(65) Prior Publication Data
US 2011/0128816 A1 Jun. 2, 2011

(30) Foreign Application Priority Data
Sep. 4, 2008 (JP) ................. 2008-227091

(51) Int. Cl.
*A61B 13/00* (2006.01)
*A61B 8/13* (2006.01)
(Continued)

(52) U.S. Cl.
CPC ............... *A61B 8/13* (2013.01); *A61B 5/0073* (2013.01); *A61B 5/0095* (2013.01); *A61B 8/483* (2013.01)

(58) Field of Classification Search
CPC .......... A61B 8/13; A61B 8/483; A61B 8/485; A61B 5/0073; A61B 5/0095
USPC .......................................... 367/7, 8, 11, 135
See application file for complete search history.

(56) References Cited

U.S. PATENT DOCUMENTS 4,730,350 A * 3/1988 Albert ............................. 378/10
5,655,536 A * 8/1997 Takamizawa ................. 600/447
(Continued)

FOREIGN PATENT DOCUMENTS

| CA | 1169145 | 6/1984 |
| CN | 1862247 | 11/2006 |

(Continued)

OTHER PUBLICATIONS

L. Xiang et al., "Listening to Light by Fast Photoacoustic Tomography Based on a Digital Phased Array System", *Proc. of SPIE*, vol. 6826, pp. 68260E-1 to-68260E-8 (2007).
(Continued)

*Primary Examiner* — Luke Ratcliffe
*Assistant Examiner* — Hovhannes Baghdasaryan
(74) *Attorney, Agent, or Firm* — Fitzpatrick, Cella, Harper & Scinto

(57) ABSTRACT

There is provided a received data processing apparatus of photoacoustic tomography including a minimum constitution unit data composition unit that sequentially reads receiving digital signals from first storage units and composes minimum constitution unit data of the acoustic wave of the minimum constitution units by performing a delay-and-sum processing. A second storage unit stores the minimum constitution unit data of the entire region of the specimen, and an image construction unit constructs an image of the specimen based on the minimum constitution unit data stored in the second storage unit. A control unit sequentially stores the minimum constitution unit data calculated by the minimum constitution unit data composition unit in the second storage unit and reads the stored minimum constitution unit data of the entire region of the specimen to transmit the minimum constitution unit data to the image construction unit.

26 Claims, 10 Drawing Sheets

(51) Int. Cl.
*A61B 5/00* (2006.01)
*A61B 8/08* (2006.01)

(56) References Cited

U.S. PATENT DOCUMENTS

| | | | | |
|---|---|---|---|---|
| 5,713,356 | A | 2/1998 | Kruger | 128/653.1 |
| 5,840,023 | A * | 11/1998 | Oraevsky et al. | 600/407 |
| 6,005,916 | A * | 12/1999 | Johnson et al. | 378/87 |
| 6,045,504 | A * | 4/2000 | Muzilla et al. | 600/437 |
| 6,309,352 | B1 * | 10/2001 | Oraevsky et al. | 600/407 |
| 7,678,048 | B1 * | 3/2010 | Urbano et al. | 600/437 |
| 7,864,307 | B2 | 1/2011 | Fukutani et al. | 356/73 |
| 7,916,283 | B2 | 3/2011 | Fukutani et al. | 356/73 |
| 7,918,797 | B2 * | 4/2011 | Bae et al. | 600/447 |
| 2001/0051772 | A1 * | 12/2001 | Bae | 600/447 |
| 2004/0019277 | A1 * | 1/2004 | Bae | 600/437 |
| 2005/0004458 | A1 | 1/2005 | Kanayama et al. | 600/437 |
| 2006/0031692 | A1 * | 2/2006 | Kato et al. | 713/300 |
| 2007/0104311 | A1 * | 5/2007 | Possin et al. | 378/19 |
| 2007/0181814 | A1 * | 8/2007 | Crosetto | 250/368 |
| 2008/0092657 | A1 * | 4/2008 | Fritsch Yusta et al. | 73/596 |
| 2008/0306371 | A1 | 12/2008 | Fukutani et al. | 600/407 |
| 2009/0198128 | A1 | 8/2009 | Fukutani et al. | 600/437 |
| 2010/0049049 | A1 | 2/2010 | Asao et al. | 600/443 |
| 2010/0053618 | A1 | 3/2010 | Nakajima et al. | 356/432 |
| 2010/0087733 | A1 | 4/2010 | Nakajima et al. | 600/437 |
| 2010/0174197 | A1 | 7/2010 | Nakajima et al. | 600/478 |
| 2010/0191109 | A1 | 7/2010 | Fukutani et al. | 600/437 |
| 2010/0331662 | A1 | 12/2010 | Fukutani et al. | 600/407 |

FOREIGN PATENT DOCUMENTS

| | | |
|---|---|---|
| EP | 1 561 424 | 8/2005 |
| JP | H02-203848 | 8/1990 |
| JP | 10-075952 | 3/1998 |
| JP | 2001-507952 | 6/2001 |
| JP | 2005-021380 | 1/2005 |

OTHER PUBLICATIONS

Office Action issued on Apr. 8, 2013, in counterpart Chinese (P.R.C.) Patent Application No. 200980133737.8, with translation.

L. Xiang et al., "Listening to Light by Fast Photoacoustic Tomography Based on a Digital Phased Array System", *Proc. Of SPIE*, vol. 6826, pp. 68260E-1-68260E-8 (2007).

EESR issued on Dec. 3, 2014 in counterpart European Patent Application No. 13188221.9.

Office Action issued on Jan. 22, 2015 in counterpart P.R. China Patent Application No. 201410002159.7, with translation.

* cited by examiner

RECEIVED DATA PROCESSING APPARATUS OF PHOTOACOUSTIC TOMOGRAPHY

TECHNICAL FIELD

The present invention relates to a received data processing apparatus of photoacoustic tomography used for a photoacoustic tomography diagnostic apparatus, and more particularly, to a technique of generating image data based on an acoustic wave receiving signal.

BACKGROUND ART

Conventionally, it has been known that, when an electromagnetic wave is irradiated to a living body, an acoustic wave is generated due to a temperature increase and thermal expansion of tissue of the living body caused by absorption of the electromagnetic wave by the living body. A technique (referred to as photoacoustic tomography (PAT)) for visualizing an inner portion of the living body in a non-invasive manner by using this phenomenon has been attracting attention and has been employed in clinical sites using photoacoustic tomography diagnostic apparatuses.

In a photoacoustic tomography diagnostic apparatus, a specimen as a target is irradiated with light, and an acoustic wave generated thereby is received by a one-dimensional or two-dimensional micro-transducer array in which a plurality of micro-transducers are arrayed. As the one-dimensional or two-dimensional micro-transducer array, probes of a kind used for an ultrasonic diagnostic apparatus generally are used.

For image reconstruction in the photoacoustic tomography, various algorithms are applied. In general, a delay-and-sum process used for the image reconstruction in the ultrasonic diagnostic apparatus may be adapted.

After the light irradiation of the specimen, although the acoustic wave generated from the target position is received during the time of receiving the acoustic wave, the distance from the target position to each of the micro-transducers is not the same (equal) for each of the micro-transducers. For this reason, the acoustic wave signal generated from the target position reaches the micro-transducers at different time points. Therefore, in general, in the photoacoustic tomography diagnostic apparatus, the time differences in the acoustic wave signals that arrive at the detectors at different time points are adjusted for by using the delay-and-sum process so as to generate the photoacoustic tomography image data corresponding to the target position. The generated data of the target position are minimum constitution units (called "pixels" or "voxels") of the two-dimensional or three-dimensional photoacoustic tomography image. In the delay-and-sum process, the acoustic wave analog signals received by the micro-transducer array are amplified by an amplifier and converted to digital signals by A/D converters, and these digital signals are stored in a storage device. Accordingly, signal values that originated from the same target position are added for all required channels.

In addition, in the photoacoustic tomography diagnostic apparatus, a process called apodization is performed in order to improve directionality of the one-dimensional or two-dimensional micro-transducer array. This process is, instead of uniformly adding the acoustic wave signals received from the micro-transducers in the micro-transducer array, rather, attenuating the acoustic wave signals that reach a region of the micro-transducer array. This process improves the directionality of the micro-transducer array by suppressing the strength of the acoustic wave signals originated in directions other than the target direction. In general, different weighting factors are applied to the acoustic wave signals received by the micro-transducers so that the same effect as applying the window functions or functions depending on solid angles and distances to the acoustic wave signals can be obtained.

In the delay-and-sum process on the digital signals, a delay apparatus for adjusting the delay times for the receiving channels is used. As the delay apparatus, a storage device such as a first in first out (FIFO) memory or a RAM is mainly used.

Recently, a large scale of a field programmable gate array (FPGA) chip has been provided. Moreover, high-speed rewritable FIFO memories or RAM memories are mounted thereon. Therefore, the FPGA chip can be easily mounted on the received data processing apparatus of photoacoustic tomography. However, the high-speed logic memories mounted on the FPGA chip have a limitation in terms of memory capacity. In addition, since large-scale FPGA chips are expensive, the received data processing apparatus of photoacoustic tomography needs to be configured with as small a logic memory capacity as possible.

Japanese Patent Application Laid-Open (JP-A) No. 2005-21380 or Japanese Patent Application National Publication (Laid-Open) No. 2001-507952 may be referred to for discussion of technologies of irradiating a specimen with light, receiving an acoustic wave generated due to thermal expansion of the specimen caused by the light irradiation, and constructing an image based on electrical signals obtained from the acoustic wave.

SUMMARY OF INVENTION

However, in the prior examples discussed in Japanese Patent Application Laid-Open No. 2005-21380 or Japanese Patent Application National Publication (Laid-Open) No. 2001-507952, there is a problem in that the configuration of a photoacoustic tomography diagnostic apparatus having multiple channels is complicated and its size is enlarged. In other words, the size of the receiving circuit is enlarged, so that the cost is increased. In addition, when a photoacoustic tomography image is reconstructed by using software, a long time is taken to acquire the photoacoustic tomography image.

The present invention has been made in view of the above problems. Since the same problems occur in the field of ultrasonic diagnostic apparatus, various solutions may be used. However, since certain features of imaging in the photoacoustic tomography diagnostic apparatus are different from those in an ultrasonic diagnostic apparatus, there exist other effective solutions using certain features.

The first different feature of imaging as between the photoacoustic tomography diagnostic apparatus and the ultrasonic diagnostic apparatus is in the time interval of the light irradiation interval and the time interval of the ultrasonic wave transmission. In the case of photoacoustic tomography, because of limitations on the light source that generates a practical light energy (several mJ or more), the light irradiation time needs to be set to a predetermined time (several tens of ms) or more. In other words, a long waiting time needs to be taken after the light irradiation. On the other hand, there is not such a limitation for an ultrasonic diagnostic apparatus. In addition, when the reception of the signal corresponding to the observation depth is completed, the next ultrasonic wave transmission needs to be performed immediately, in order to improve the frame rate. The time interval of the ultrasonic wave transmission is at most several hundreds of μs.

The second different feature of imaging as between the photoacoustic tomography diagnostic apparatus and the ultrasonic diagnostic apparatus is the difference in the observation depth and the reception time associated with the observation depth. In a photoacoustic tomography diagnostic apparatus, since light attenuation in the human body is very high, the observation depth is limited to several cm. On the other hand, with an ultrasonic diagnostic apparatus, the observation depth may be set to several tens of cm. Therefore, in photoacoustic tomography, the time of acquiring the receiving data after the light irradiation may be several tens of μs. However, in the ultrasonic diagnostic apparatus, when the depth of several tens of cm is observed, the time of acquiring the receiving data may be several hundreds of μs. For example, when the depth of 20 cm is observed, the time of acquiring the receiving data is about 260 μs.

In the ultrasonic diagnostic apparatus, since the next transmission is performed immediately upon the elapse of the time required for acquiring the receiving data, the generation of the image data involves performing the delay-and-sum process during reception, in order to maintain real-time characteristics. In this case, since the data incoming into the receiving channels need to be processed simultaneously, if the number of receiving channels is increased, the size of the apparatus is enlarged, and its cost likewise is increased.

On the other hand, in the photoacoustic tomography diagnostic apparatus, the light irradiation interval is long, and the time of acquiring the receiving data is short. In other words, a long waiting time is taken. Therefore, once the receiving data is stored in a storage medium, the generation of the image data can be performed in a sufficient time. This means that the image data can be generated in a time division manner by a miniaturized receiving data processing circuit. Since the real-time characteristics of the photoacoustic tomography image are rate-controlled by the light irradiation time, if the image data can be generated in the waiting time, the real-time characteristics of the image are not diminished.

The purpose of the present invention is to provide a received data processing apparatus of photoacoustic tomography having a novel structure capable of performing photoacoustic tomography image reconstruction by a miniaturized configuration at a high speed by using the aforementioned features of the photoacoustic tomography.

In order to accomplish the purpose, the present invention is configured as follows. A received data processing apparatus of photoacoustic tomography of receiving an acoustic wave generated by irradiating a specimen with light and constructing an image from an electrical signal obtained from the received acoustic wave, including a plurality of electrical signal conversion means that digitize received signals from a plurality of acoustic wave detectors that receive the acoustic wave originated from a specimen region, and a plurality of first storage means that stores received digital signals digitized by the electrical signal conversion means. Minimum constitution unit data composition means sequentially reads the received digital signals originated from minimum constitution units, which partition the specimen region, from the plurality of the first storage means, based on delay information of the acoustic waves assuming that the acoustic waves reach the respective acoustic wave detectors from the respective minimum constitution units, and composes minimum constitution unit data, which is acoustic wave data of the respective minimum constitution unit, by performing a delay-and-sum process. Second storage means stores the minimum constitution unit data of the entire region of the specimen, and image construction means constructs an image of the region of the specimen based on the minimum constitution unit data stored in the second storage means. Control means sequentially stores the minimum constitution unit data composed by the minimum constitution unit data composition means in the second storage means, and reads the stored minimum constitution unit data of the entire specimen region, and transmits the minimum constitution unit data to the image construction means.

According to the present invention, photoacoustic tomography image reconstruction can be performed by a miniaturized configuration at a high speed.

Further features of the present invention will become apparent from the following description of exemplary embodiments with reference to the attached drawings.

DESCRIPTION OF EMBODIMENTS

Hereinafter, embodiments of the present invention will be described in detail with reference to the accompanying drawings.

First Embodiment

Figure 1:
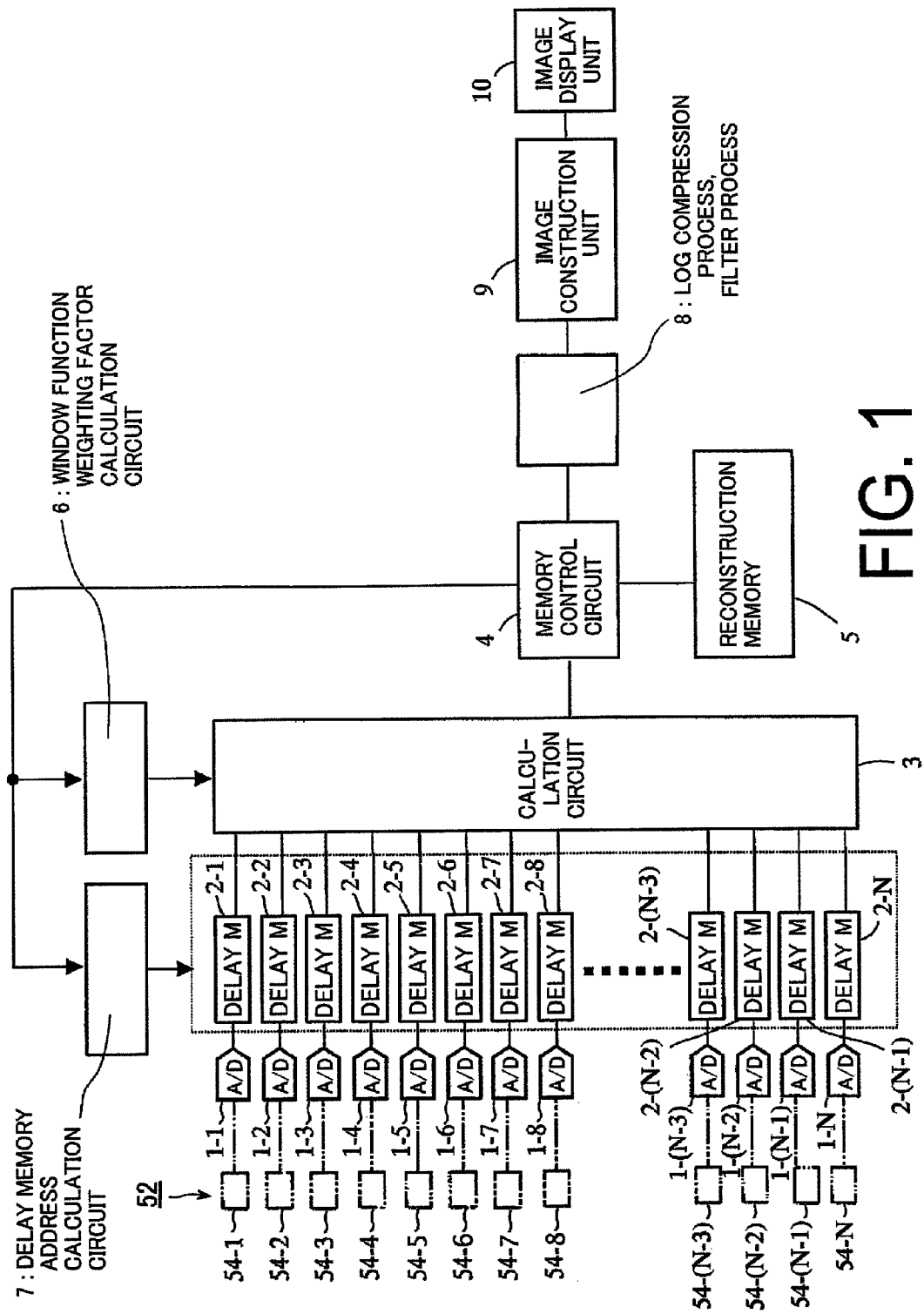
FIG. 1 is a block diagram illustrating a received data processing apparatus of photoacoustic tomography according to a first embodiment of the present invention.

FIG. 1 is a view illustrating a received data processing apparatus of photoacoustic tomography according to a first embodiment of the present invention. In FIG. 1, the total number of channels of the received data processing apparatus of photoacoustic tomography is N.

The received data processing apparatus of photoacoustic tomography forms an image based an electrical signal obtained by irradiating a specimen with light and receiving an acoustic wave generated from localized thermal expansion and contraction of the specimen as a result of the light irradiation.

The apparatus includes N A/D converters 1-1 to 1-N, N delay adjustment memories (DELAY M) 2-1 to 2-N, and a calculation circuit 3. In addition, the apparatus further includes a memory control circuit 4, a reconstruction memory 5, a window function weighting factor calculation circuit 6, a delay memory address calculation circuit 7, a signal processing block 8 (log compression process, filter process), an image construction unit 9, and an image display unit 10.

The A/D converters 1-1 to 1-N are electrical signal conversion units that digitize analog electrical signals received by acoustic wave detectors 54-1 to 54-N of an acoustic wave detector array 52. The acoustic wave detector array 52 constitutes a receiving unit that allows the N acoustic wave detectors 54-1 to 54-N to receive an acoustic wave originated from a specimen region as a to-be-processed target and converts the received acoustic wave to the analog electrical signal.

The delay adjustment memories 2-1 to 2-N are first storage units that store the receiving digital signal digitized by the A/D converters 1-1 to 1-N in a time sequence.

The calculation circuit 3 is a minimum constitution unit data composition unit that reads receiving digital signals originated from voxels that are minimum constitution units of the specimen region as a target, from the plurality of delay adjustment memories 2-1 to 2-N, to compose voxel data. The respective voxel data are the acoustic wave data of each respective minimum constitution unit. The receiving digital signals originated from the voxels are read according to delay information on the acoustic wave from the voxels to reach the acoustic wave detectors 54-1 to 54-N, and a delay-and-sum process is performed on the read receiving digital signal.

Figure 2:
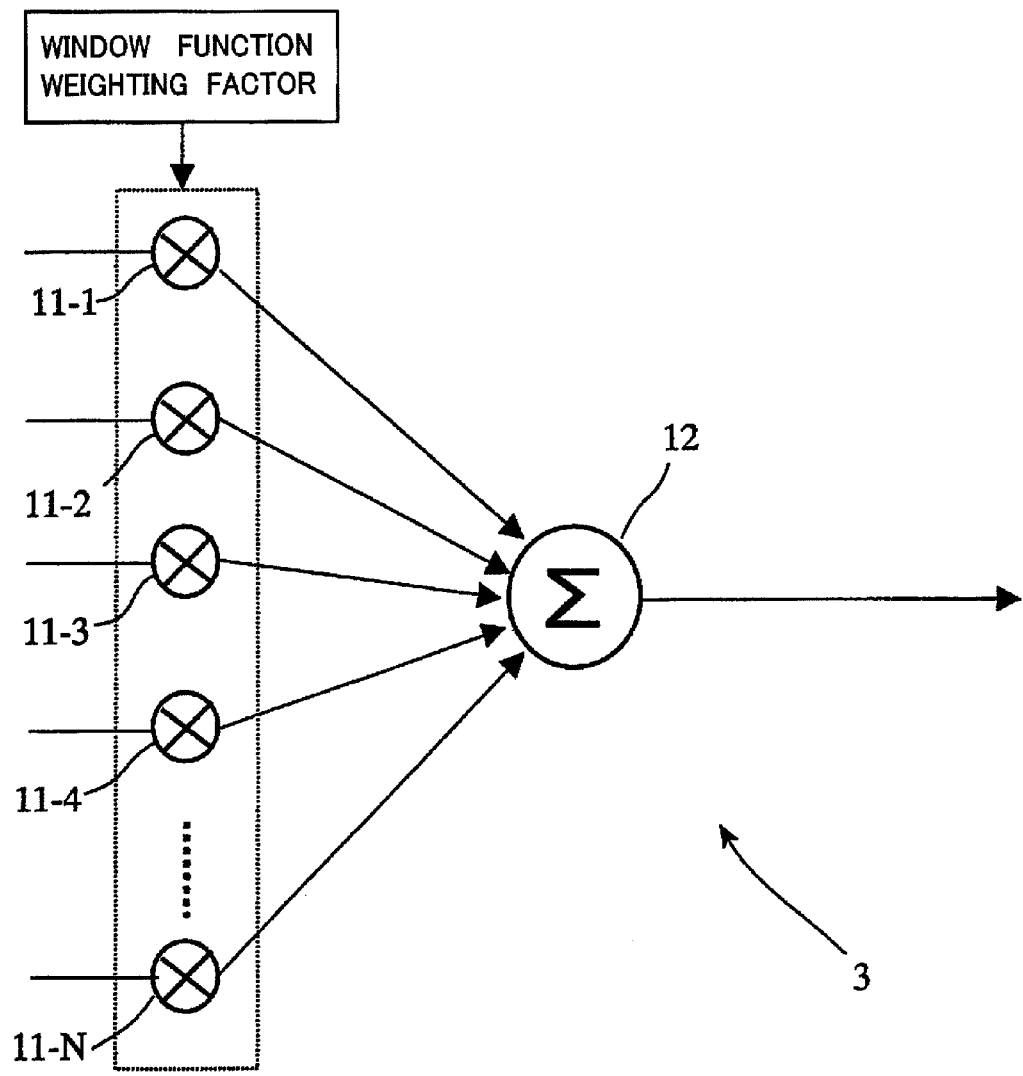
FIG. 2 is a view illustrating a configuration of a calculation circuit according to the first embodiment of the present invention.

As shown in FIG. 2, the calculation circuit 3 includes N multipliers 11-1 to 11-N and one addition circuit 12. In addition, a plurality of the addition circuits 12 may be included in the calculation circuit 3.

The reconstruction memory 5 is a second storage unit that can store voxel data of the entire region of the specimen.

The image construction unit 9 is a unit that constructs an image of the specimen region based on the voxel data stored in the reconstruction memory 5.

In addition, the memory control circuit 4 is a control unit that sequentially stores the voxel data calculated by the calculation circuit 3 in the reconstruction memory 5, which is a second storage unit, and reads the stored voxel data of the entire region of the specimen to transmit the voxel data to the image construction unit 9.

The delay memory address calculation circuit 7 is an address calculation unit that calculates delay times that are taken for the acoustic wave from the voxels to reach the acoustic wave detectors 54-1 to 54-N based on the voxel coordinates that are the minimum constitution unit coordinates in the specimen region. In addition, addresses in which receiving digital signals originated from the voxels corresponding to the delay times are stored to the delay memories 2-1 to 2-N.

The window function weighting factor calculation circuit 6 is a window function weighting factor calculation unit that calculates the window function weighting factors of the receiving channels through which the receiving signals of the acoustic waves are transmitted based on the voxel coordinates in the specimen region as a target and applies the calculated window function weighting factor to the calculation circuit 3.

In the present embodiment, the signal processing block 8 is a second signal processing unit that performs signal processes including filter processes such as low-pass filtering and high-pass filtering, a logarithm compression (log compression) process, a differentiation process, an envelope detection process, and a quadrature detection process. The signal processing block 8 shown in FIG. 1 performs signal processing on the composed minimum constitution unit data. In this case, log compression processing and filter processing are featured in particular.

Next, the operations according to the first embodiment are described in detail.

Light such as a laser beam is provided from a light source (not shown) and used to irradiate the specimen, and as a result, tissue of the specimen is locally made to expand and contract thermally, so that the acoustic wave is generated. The acoustic wave is received by the N acoustic wave detectors 54-1 to 54-N of the acoustic wave detector array 52 to be converted to analog electrical signals. The analog electrical signals are digitized by the N A/D converters 1-1 to 1-N, so that N digital signals are output to the N delay adjustment memories (DELAY M) 2-1 to 2-N.

The delay adjustment memories (DELAY M) 2-1 to 2-N store digital signals output from the A/D converters 1-1 to 1-N, respectively.

The delay memory address calculation circuit 7 calculates the delay times and the delay adjustment memory addresses corresponding to the target voxels based on the voxel coordinates in the specimen region as a target and designates the delay adjustment memory addresses to the delay adjustment memories 2-1 to 2-N. The receiving digital data originated from the minimum constitution units in the specimen region, namely, originated from the target voxels, are read from the delay adjustment memories 2-1 to 2-N according to the delay adjustment memory addresses calculated by the delay memory address calculation circuit 7. Next, the receiving digital data that are read out are output to the multipliers 11-1 to 11-N of the calculation circuit 3.

Figure 3:
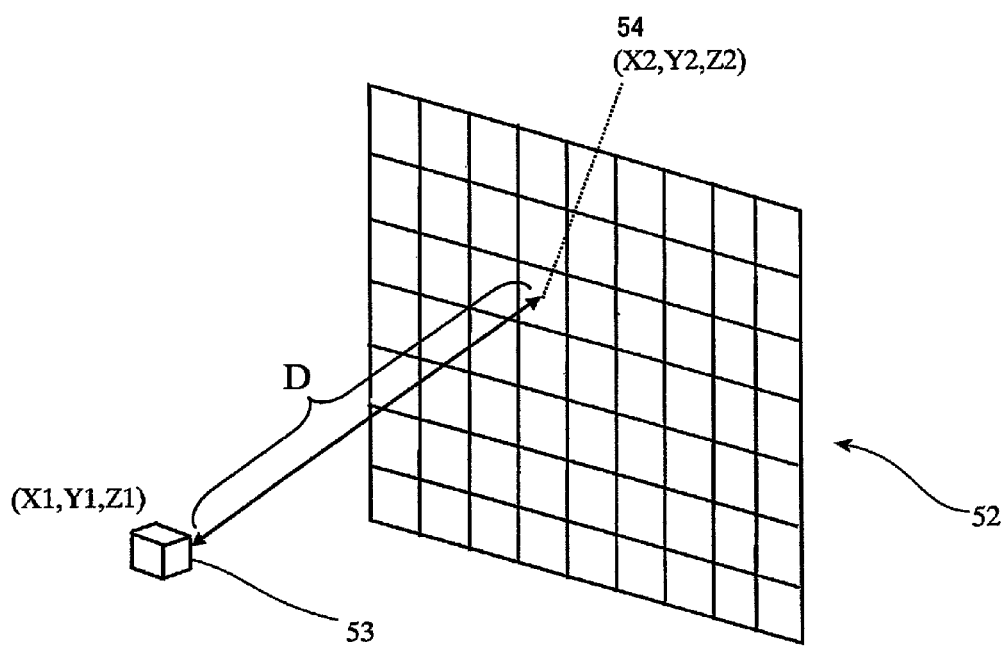
FIG. 3 is a view illustrating a positional relationship between a target voxel and an acoustic wave detector array in a specimen region.

FIG. 3 illustrates an example of a positional relationship among a target voxel 53 in a specimen region as a target, an acoustic wave detector array 52, and an acoustic wave detector 54 in the array. If the coordinates (X1, Y1, Z1) of the target voxel 53 and the coordinates (X2, Y2, Z2) of the acoustic wave detector 54 in the array are determined in a predetermined coordinate system, the distance D between the target voxel 53 and the acoustic wave detector 54 in the array is immediately obtained by means of the Pythagorean theorem.

In addition, an acoustic wave reaching time (delay time) from the target voxel 53 to the acoustic wave detector 54 in the array is calculated by dividing the distance D between the target voxel 53 and the acoustic wave detector 54 in the array by the velocity of sound in the intervening matter.

In addition, while the acoustic wave is received from the specimen region as a target, the delay adjustment memories 2-1 to 2-N sequentially store the digital data originated from the acoustic wave in the addresses in the delay adjustment memories 2-1 to 2-N in a time sequence according to a predetermined rule. In other words, from the time of the light irradiation, the receiving digital signals are read in time sequence manner from the delay adjustment memories 2-1 to 2-N, and the acoustic wave signals that reach by the delay times according to the distances from the positions of the voxels in which the acoustic wave is generated are stored in the delay adjustment memories 2-1 to 2-N.

The delay adjustment memory address can be specified based on the acoustic wave reaching time (delay time) that is taken for the acoustic wave from the target voxel 53 to reach the acoustic wave detectors 54-1 to 54-N in the array and the rule of storing the digital data in the delay adjustment memories 2-1 to 2-N. The delay memory address is a memory address in which digital data that originated from a target voxel exists.

In the present embodiment, the delay memory address calculation circuit 7 calculates the delay adjustment memory addresses of the target voxels and designates the calculated delay adjustment memory addresses for the respective delay adjustment memories 2-1 to 2-N. The delay adjustment memories 2-1 to 2-N output the digital data originated from the minimum constitution units, namely, originated from the target voxels to the calculation circuit 3 according to the delay adjustment memory addresses designated by the delay memory address calculation circuit 7.

The window function weighting factor calculation circuit 6 calculates the window function weighting factors corresponding to the target voxels based on the voxel coordinates in the specimen region as a target and applies the window function weighting factors to the calculation circuit 3. Since the receiving digital signals output from the delay adjustment memories 2-1 to 2-N are in the apodization, the channels are applied with the window function weighting factors calculated by the window function weighting factor calculation circuit 6, and the receiving digital signals are output to the addition circuit 12.

The addition circuit 12 adds the receiving digital signals of all channels applied with the window function weighting factors. As a result of this processing, the receiving digital signals that are acoustic wave receiving signal information that originated from the target voxels are delayed appropriately and summed.

The delayed-and-summed target voxel data are stored in the reconstruction memory 5 by the memory control circuit 4. The process is repetitively performed for all the voxels, so that all the voxel data in the specimen region being taken as a target are sequentially delayed-and-summed and stored in the reconstruction memory 5.

Once all the voxel data in the target region of the specimen are delayed-and-summed and stored in the reconstruction memory 5, the memory control circuit 4 outputs the voxel data to the signal processing block 8 (log compression processing, filter processing) as a second signal processing unit. The signal processing block 8 (log compression processing, filter processing) performs signal processes such as a log compression process and a filtering process on the input voxel data and outputs the result thereof to the image construction unit 9. The signal processes may include filtering processes such as a low-pass filtering process and a high-pass filtering process, a log compression process, a differentiation process, an envelope detection process, and a quadrature detection process. In addition, although not shown, a second parameter calculation unit that calculates a parameter required for the signal processing and applies the parameter to the signal processing block 8 may be included.

The image construction unit 9 constructs the photoacoustic tomography image based on the voxel data on which the signal processing is performed and outputs the image to the image display unit 10. The image display unit 10 displays the constructed photoacoustic tomography image. These are a series of the operations according to the first embodiment.

In the case of the photoacoustic tomography, because of limitations on the light source that generates a practical light energy (several mJ or more), the light irradiation time needs to be set to be a predetermined time or more. In the present embodiment, the photoacoustic tomography receiving data is formed using the light irradiation interval, that is, the waiting time that precedes the next illumination. Therefore, if the generation of all the voxel data in the specimen target region is ended before the next light irradiation starts, the real-time characteristics of the photoacoustic tomography imaging are maintained, and are not diminished by the operations of the present embodiment.

In the photoacoustic tomography, when the S/N ratio of the acoustic wave generated from light irradiation to the specimen is low, there is a need to perform an addition averaging process on the receiving signals multiple times so as to improve the S/N ratio. In this case, an addition averaging process may be performed on the delayed-and-summed data of the target voxels, that is, the minimum constitution unit data obtained by multiple times of reception, by using the memory control circuit 4 and the reconstruction memory 5. In this case, the memory control circuit 4 serves as the addition averaging unit.

According to the configuration just described, the addition averaging processing is performed at the time when all the processes are ended, so that the target voxel data having improved S/N ratio is stored in the reconstruction memory 5.

The type of memories used as the delay adjustment memories 2-1 to 2-N and the reconstruction memory 5 is not particularly limited. These memories may be configured by using FIFO (first-in first-out) memories or RAMs (not shown). If capable of being suitably adapted, other types of storage units may be used.

In addition, the signal processing block 8 (log compression process, filter process) is not necessarily disposed just before the image construction unit 9 as shown in FIG. 1. If needed, the signal processing block 8 may be disposed at any position in the received data processing apparatus of photoacoustic tomography. In addition, the only one signal processing block 8 is not necessarily disposed. For example, the signal processing block 8 may be disposed in the calculation circuit 3 or for each channel of the acoustic wave detectors. In addition, one signal processing block 8 may be disposed at the output portion of each of the delay adjustment memories 2-1 to 2-N for each channel (not shown). When a block such as signal processing block 8 is provided for each receiving channel, those signal processing blocks 8 correspond to the first signal processing units according to the present invention. In this case, a first parameter calculation unit that calculates an independent parameter required for the signal process for each channel and applies the parameter may be included (not shown). In addition, the second signal processing unit and the first signal processing unit may be the same unit.

In addition, the calculation circuit 3 is not necessarily designed to perform only multiplication processing and addition processing as shown in FIG. 2. If needed, a calculation unit and a signal processing unit required for performing photoacoustic tomography image reconstruction may be further included (not shown). In addition, a unit that calculates an independent parameter required for performing the signal processing for each channel and applies the parameter may be included (not shown). In this case, a parameter calculation unit may be disposed in the calculation circuit 3. Otherwise, separate calculation blocks may be provided to apply the calculated parameter to the calculation circuit 3 (not shown).

In addition, a mounting unit for the received data processing apparatus of photoacoustic tomography is not necessarily limited to an FPGA. If needed, the apparatus can be configured by combining a digital signal processor (DSP), a general purpose CPU, various volatile memories, and various nonvolatile memories (not shown).

In addition, the acoustic wave detector array 52 is not necessarily a 2D array as shown in FIG. 3. For example, a 1D or 1.5D array may be used (not shown). In addition, as a shape of a probe of a general ultrasonic diagnostic apparatus, there are various shapes such as a linear shape, a sector shape, and a convex shape. However, the present invention is not necessarily limited by the shape of the probe used in the acoustic wave reception.

In addition, the method of implementing the image construction unit 9 is not particularly limited. A general purpose CPU or GPU may be used. Otherwise, other suitable units may be used.

Next, other embodiments of the present invention will be described. In the description hereinafter, elements different from those of the first embodiment and the foregoing embodiment are mainly described. In addition, the similar elements are denoted by the same reference numerals, and the description thereof will not be repeated.

Second Embodiment

Figure 4:
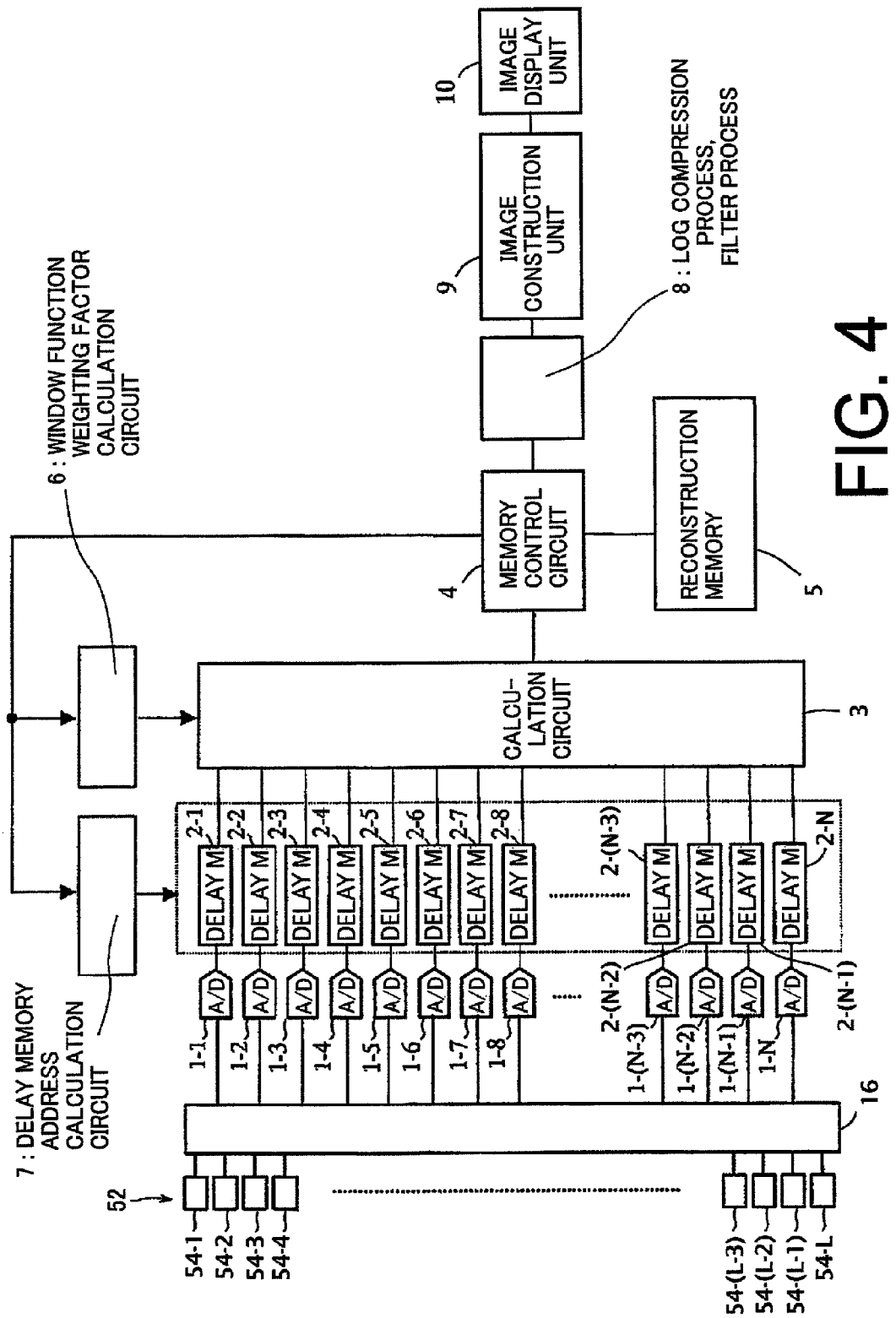
FIG. 4 is a block diagram illustrating a received data processing apparatus of photoacoustic tomography according to a second embodiment of the present invention.

FIG. 4 is a view illustrating a received data processing apparatus of photoacoustic tomography according to a second embodiment of the present invention. In FIG. 4, the number of acoustic wave detectors is L, and the total number of channels of the received data processing apparatus of photoacoustic tomography is N. In this case, L>N, that is, the number of acoustic wave detectors is larger than the total number of channels of the received data processing apparatus of photoacoustic tomography.

The received data processing apparatus of photoacoustic tomography includes N A/D converters 1-1 to 1-N, N delay adjustment memories (DELAY M) 2-1 to 2-N, and a calculation circuit 3. In addition, the apparatus further includes a memory control circuit 4, a reconstruction memory 5, a window function weighting factor calculation circuit 6, a delay memory address calculation circuit 7, a signal processing block 8 (log compression process, filter process) that performs a log compression process and a filter process, an image construction unit 9, and an image display unit 10. In addition, between the acoustic wave detectors 54-1 to 54-L and the A/D converters 1-1 to 1-N, a switching circuit 16 as a connection switching unit of switching connection states therebetween is disposed.

Next, the operations of the second embodiment are described.

The operations of the circuits following the N A/D converters 1-1 to 1-N are basically the same as those as the first embodiment. However, unlike the first embodiment, the connection states between the acoustic wave detectors 54-1 to 54-L and the A/D converters 1-1 to 1-N can be switched by the switching circuit 16.

Figure 5:
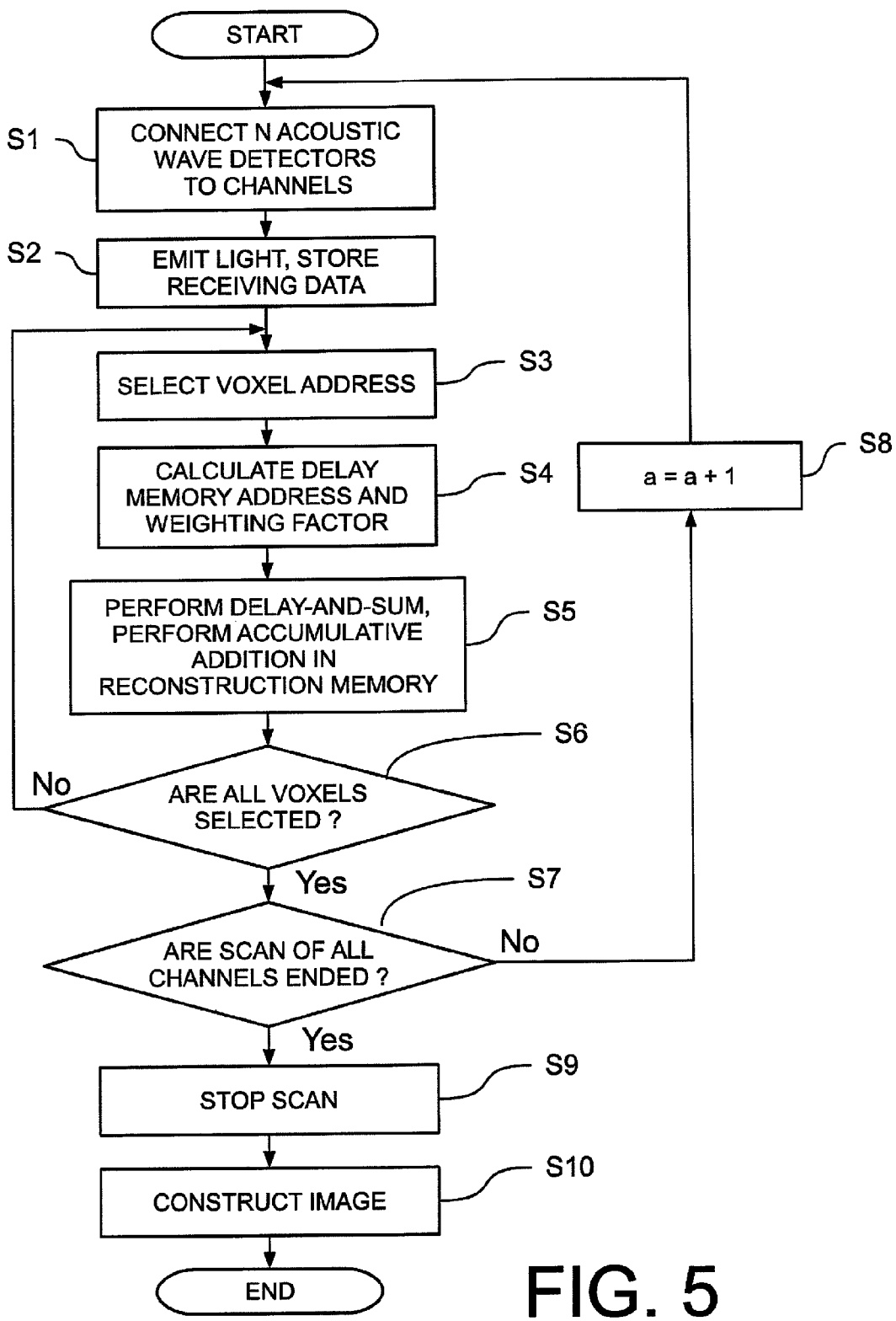
FIG. 5 is a flowchart illustrating operations of the received data processing apparatus of photoacoustic tomography according to the second embodiment of the present invention.

FIG. 5 is a flowchart illustrating the operations according to the second embodiment.

Firstly, N acoustic wave detectors (a, a+1, a+2, ..., a+N−1) that are selected among the L acoustic wave detectors 54-1 to 54-L are connected to the N channels of the received data processing apparatus of photoacoustic tomography (refer to step S1).

Next, the target region of the specimen is irradiated with light, and the acoustic wave generated therefrom is received and digitized by the A/D converters 1-1 to 1-N. The digitized receiving data are stored in the N delay adjustment memories 2-1 to 2-N (refer to step S2).

Next, the target voxel on which the delay-and-sum process is to be performed is determined (refer to step S3), and the delay memory address and the weighting factor required for the delay-and-sum process are calculated (refer to step S4). Next, the weighting factor is applied to the data read from the delay storage M according to the calculated delay memory address, the delay-and-sum process is performed, and the result thereof is stored in the reconstruction memory 5 (refer to step S5).

Once the delay-and-sum processing on the selected target voxel is ended, it is determined whether the processing of all the voxels is completed. If not, the procedure returns to step S3 to select the next target voxel, perform the delay-and-sum processing, and the result thereof is accumulatively added in the reconstruction memory 5. This procedure is repeated until the delay-and-sum processing on all the voxels of the target region is ended. At this time, the delay-and-sum processing on the target voxels is ended based on the acoustic wave received from the initially selected acoustic wave detector group (a, a+1, a+2, ..., a+N−1).

Next, the N acoustic wave detectors to be selected are changed.

FIG. 5 illustrates an example where acoustic wave detectors (a+1, a+2, ..., a+N) are newly selected among the L acoustic wave detectors (refer to steps S8 and S1). Next, a target region of the specimen is irradiated with light, and an acoustic wave generated therefrom is received by using the newly-selected N acoustic wave detectors (a+1, a+2, ..., a+N). Next, the voxel data as the minimum constitution unit data that are sequentially obtained in a time division manner by performing the delay-and-sum processing on all the voxels of the target region are accumulatively added in the same voxel data of the reconstruction memory 5 (refer to steps S2 to S5).

The process is repeated until all the acoustic wave detectors 54-1 to 54-L in which reception is to be performed have been selected and the delay-and-sum processing on all the target voxels is ended (S7). If reception scanning of all the acoustic wave detectors 54-1 to 54-L is ended, the reception scan is ended (refer to step S9), and the voxel data stored in the reconstruction memory 5 are read to be transmitted to the image construction unit (refer to step S10).

By using the aforementioned procedures, the reception can be performed in the configuration where the reception region is changed and divided in the array of the acoustic wave detectors 54-1 to 54-L. An advantage of this procedure is to reconstruct the photoacoustic tomography image by using a smaller number of channels (N) of the received data processing apparatus of photoacoustic tomography than the number of acoustic wave detectors (L) in the acoustic wave detector array 52.

In addition, the same target voxel data may be received from different reception regions in the acoustic wave detectors 54-1 to 54-L. In this case, in the memory control circuit 4 and the reconstruction memory 5, an accumulative addition process or an addition averaging process is performed on the same target voxel data to generate the target voxel data. When the reception regions in the array of the acoustic wave detectors 54-1 to 54-L are different, the weighting factors that the multipliers 11-1 to 11-N of the calculation circuit 3 designate for the receiving data may be changed.

In the present embodiment, the memory control circuit 4 and the reconstruction memory 5 are provided in order to process and store the target voxel data, so that all the acoustic wave detectors need not be simultaneously connected to the received data processing apparatus of photoacoustic tomography. In other words, the received data processing apparatus of photoacoustic tomography can be miniaturized.

Herein, the reception region selection scheme of the acoustic wave detectors 54-1 to 54-L is not necessarily the same as that shown in FIG. 5, but may be suitably determined as needed. In addition, the relationship between the number L of acoustic wave detectors and the number N of channels of the received data processing apparatus of photoacoustic tomography is not necessarily limited to L>N. Furthermore, it is not necessary that all the channels of the received data processing apparatus of photoacoustic tomography are used during reception.

In addition, a switching circuit as a connection switching unit of switching connection states between the A/D converters 1 and the delay adjustment memories 2 may be disposed, so that the acoustic wave can be received while the connection states between the A/D converters 1 and the delay adjustment memories 2 are sequentially switched (not shown). For example, when the total number of A/D converters 1 is L and the total number of delay adjustment memories 2 is N (L>N), the connection states between the A/D converters 1 and the delay adjustment memories 2 are sequentially switched each reception. In addition, all the A/D converters 1 in which the reception is to be performed are selected, so that the processes are continuously performed until the delay-and-sum processing for the target voxels is ended.

In this manner, the acoustic wave may be configured to be received while the connection states between the A/D converters 1 and the delay adjustment memories 2 and the connection states between the acoustic wave detector array 52 and the A/D converters 1 are sequentially switched.

In the case of photoacoustic tomography, because of limitations on the light source, the light irradiation time needs to be set to a predetermined time or more, as stated previously. In the present embodiment, the photoacoustic tomography receiving data is formed using the light irradiation interval, that is, the waiting time that must exist before the next illumination can be begun. Therefore, if the generation of all the voxel data in the specimen target region is ended before the next light irradiation starts, the real-time characteristics of the photoacoustic tomography image are maintained, and are not diminished by the operations of the present embodiment.

Due to the switching circuit 16 disposed between the acoustic wave detector array 52 and the A/D converters 1, the apparatus can be configured with a smaller number of A/D converters than of acoustic wave detectors. In addition, due to the switching circuit disposed between the A/D converters 1 and the delay adjustment memories 2, the apparatus can be configured with a smaller number of delay adjustment memories than of the A/D converters, as explained above.

In addition, the signal processing block 8 (log compression process, filter process) that performs the log compression processing and filter processing is not necessarily disposed just before the image construction unit 9 as shown in FIG. 4. If needed, the signal processing block 8 may be disposed in the calculation circuit 3. In addition, such a signal processing block 8 may be provided for each N channel connected to the calculation circuit 3 from the switching circuit 16. In addition, even the illustrated one signal processing block 8 is not necessarily provided as a separate unit, but, for example, the signal processing block 8 may be disposed in the calculation circuit 3 or at the output portions of each of the delay adjustment memories 2-1 to 2-N for each channel (not shown). In this case, a parameter required for the signal processing is calculated for each channel to be applied (not shown).

Third Embodiment

Figure 6:
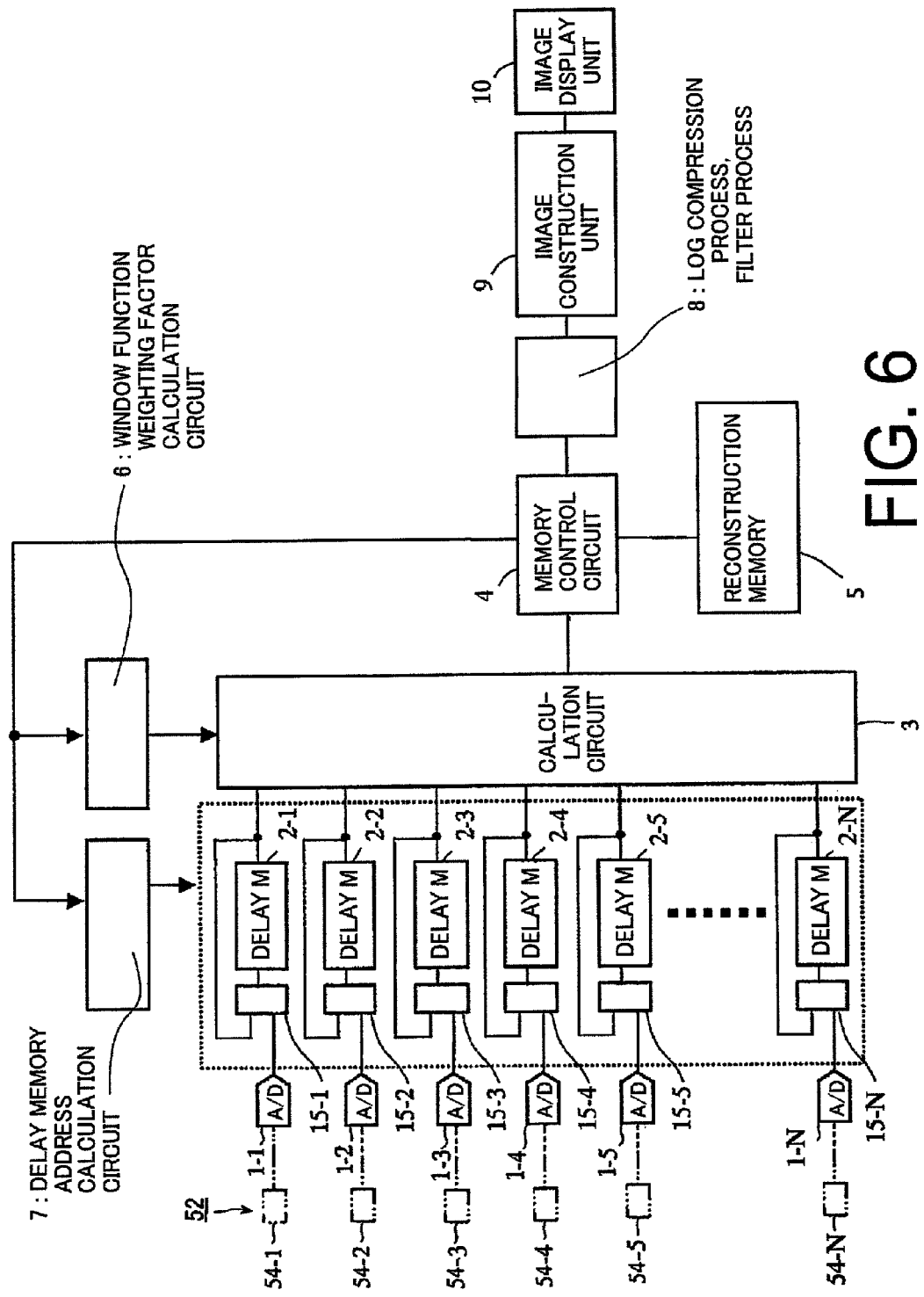
FIG. 6 is a block diagram illustrating a received data processing apparatus of photoacoustic tomography according to a third embodiment of the present invention.

FIG. 6 is a view illustrating a received data processing apparatus of photoacoustic tomography according to a third embodiment of the present invention. In FIG. 6, the total number of channels of the received data processing apparatus of photoacoustic tomography is N.

The received data processing apparatus of photoacoustic tomography includes N A/D converters 1-1 to 1-N, addition averaging circuits 15-1 to 15-N, N delay adjustment memories (DELAY M) 2-1 to 2-N, and a calculation circuit 3. In addition, the apparatus further includes a memory control circuit 4, a reconstruction memory 5, a window function weighting factor calculation circuit 6, a delay memory address calculation circuit 7, a signal processing block 8 (log compression processing, filter processing), an image construction unit 9, and an image display unit 10.

The third embodiment is different from the first and second embodiments in that the addition averaging circuits 15-1 to 15-N as addition processing units are included. In addition, instead of the addition averaging process, an accumulative addition process may be performed.

Next, the operations according to the third embodiment are described. The operations of the N A/D converters 1-1 to 1-N and the operations of the circuits following the calculation circuit 3 are basically the same as those of the first and second embodiments. However, unlike the first and second embodiments, the delay adjustment memories 2-1 to 2-N cooperate with the addition averaging circuits 15-1 to 15-N to perform the addition averaging processing or the accumulative addition processing on the receiving digital signal.

In photoacoustic tomography, when the S/N ratio of the acoustic wave generated from light irradiation of the specimen is low, there is a need to perform an addition averaging process or accumulative addition process on the receiving signal. In the third embodiment, the addition averaging circuits 15-1 to 15-N cooperate with the delay adjustment memories 2-1 to 2-N to store the addition-averaging-processed or accumulative-addition-processed receiving data in the delay adjustment memories 2-1 to 2-N. Moreover, the delay-and-sum processing is performed on the target voxel data. According to the third embodiment, target voxel data having an improved S/N ratio can be obtained.

In the case of photoacoustic tomography, because of limitations on the light source, the light irradiation time needs to be set to be a predetermined time or more. In the present embodiment, the formation of the photoacoustic tomography receiving data is performed using the light irradiation interval, that is, the waiting time prior to the next illumination. Therefore, after light irradiation is performed multiple times to perform the addition averaging process, if the generation of all the voxel data in the specimen target region is ended before the next light irradiation starts, the real-time characteristics of the photoacoustic tomography image processing are maintained and are not diminished.

In addition, in the third embodiment, a switching circuit may be disposed between the A/D converter 1 and the addition averaging circuit, and the acoustic wave may be received while the connection states between the A/D converter 1 and the addition averaging circuit are sequentially switched (not shown). For example, when the total number of A/D converters is L and the total number of addition averaging circuits is N (L>N), the connection states between the A/D converters and the addition averaging circuits are sequentially switched every reception. In addition, the A/D converters in which reception is to be performed are selected, so that the processes are continuously performed until the delay-and-sum processing for all the target voxels is ended. In this manner, the switching circuit as a control unit that switches between the addition averaging circuits and the A/D converters is provided, so that the apparatus can be configured with a smaller number of addition averaging circuits and of delay adjustment memories than of A/D converters.

In addition to the illustrated configuration, similarly to the second embodiment, as shown in FIG. 4, a switching circuit may be disposed between the acoustic wave detector array and the A/D converters (not shown). Due to the switching circuit disposed between the acoustic wave detector array and the A/D converters, the apparatus can be configured with a smaller number of A/D converters than of the acoustic wave detectors in the array.

In this manner, it can be arranged that the acoustic wave is received while the connection states between the A/D converters and the addition averaging circuits and between the A/D converters and the delay adjustment memories and the connection states between the acoustic wave detector array and the A/D converters are sequentially switched.

In addition, in the configuration of the present embodiment, as described in connection with the first embodiment, the addition averaging processing may also be performed on the delayed-and-summed data obtained in multiple times of reception, by using the memory control circuit 4 and the reconstruction memory 5.

Fourth Embodiment

Figure 7:
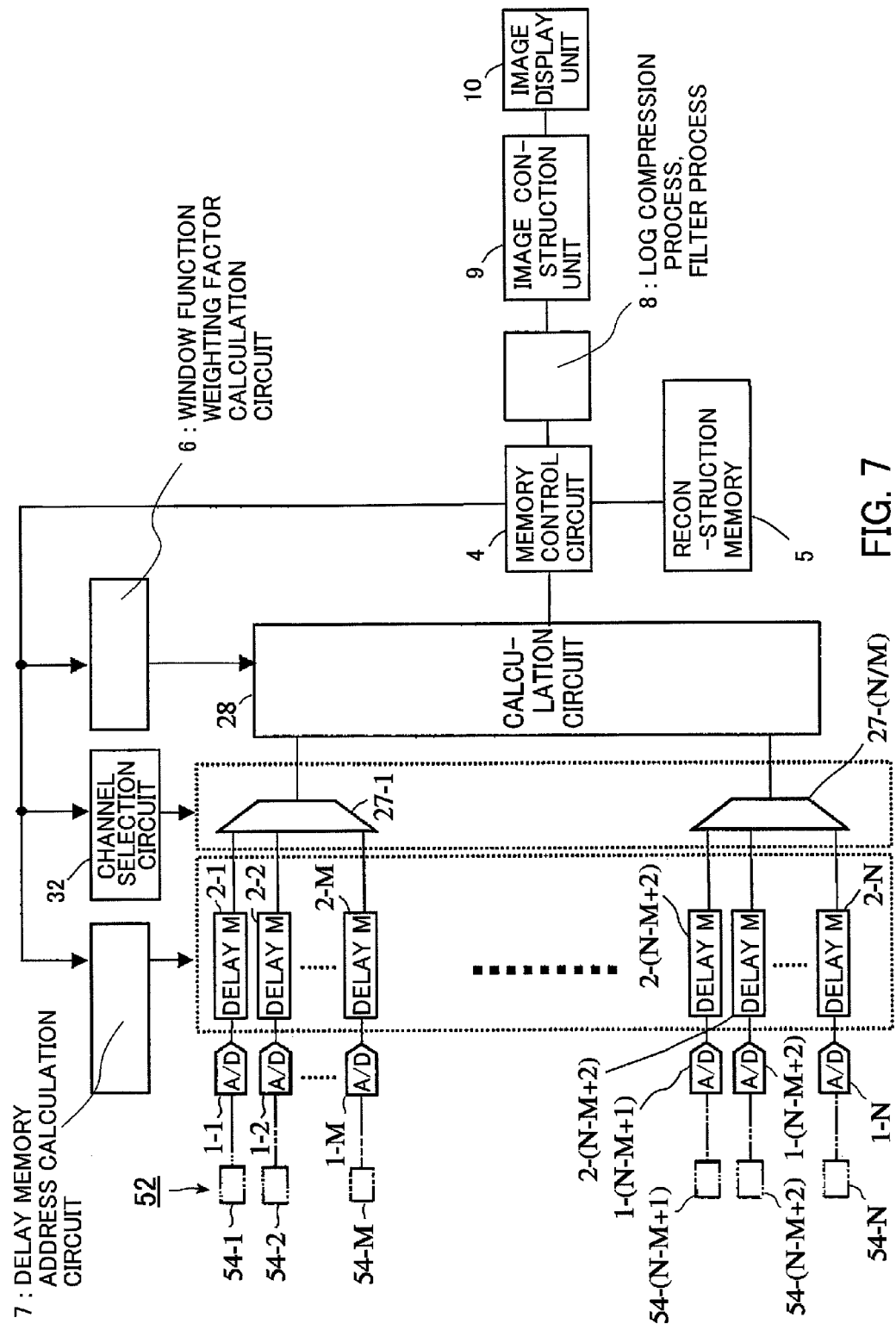
FIG. 7 is a block diagram illustrating a received data processing apparatus of photoacoustic tomography according to a fourth embodiment of the present invention.

FIG. 7 is a view illustrating a received data processing apparatus of photoacoustic tomography according to a fourth embodiment of the present invention. In FIG. 7, the total number of channels of the received data processing apparatus of photoacoustic tomography is N.

The received data processing apparatus of photoacoustic tomography includes N A/D converters 1-1 to 1-N, N delay adjustment memories (DELAY M) 2-1 to 2-N, and a calculation circuit 28. In addition, the apparatus further includes a memory control circuit 4, a reconstruction memory 5, a window function weighting factor calculation circuit 6, a delay memory address calculation circuit 7, a signal processing block 8 (log compression processing, filter processing), an image construction unit 9, and an image display unit 10.

In the fourth embodiment, memory selecting switches 27-1 to 27-(N/M) are disposed between the delay adjustment memories 2-1 to 2-N and the calculation circuit 3. In addition, N/M groups of M delay adjustment memories each are connected to the memory selecting switches 27-1 to 27-(N/M), so that the memory selecting switches 27-1 to 27-(N/M) are configured to be selected by the channel selection circuit 32.

Figure 8:
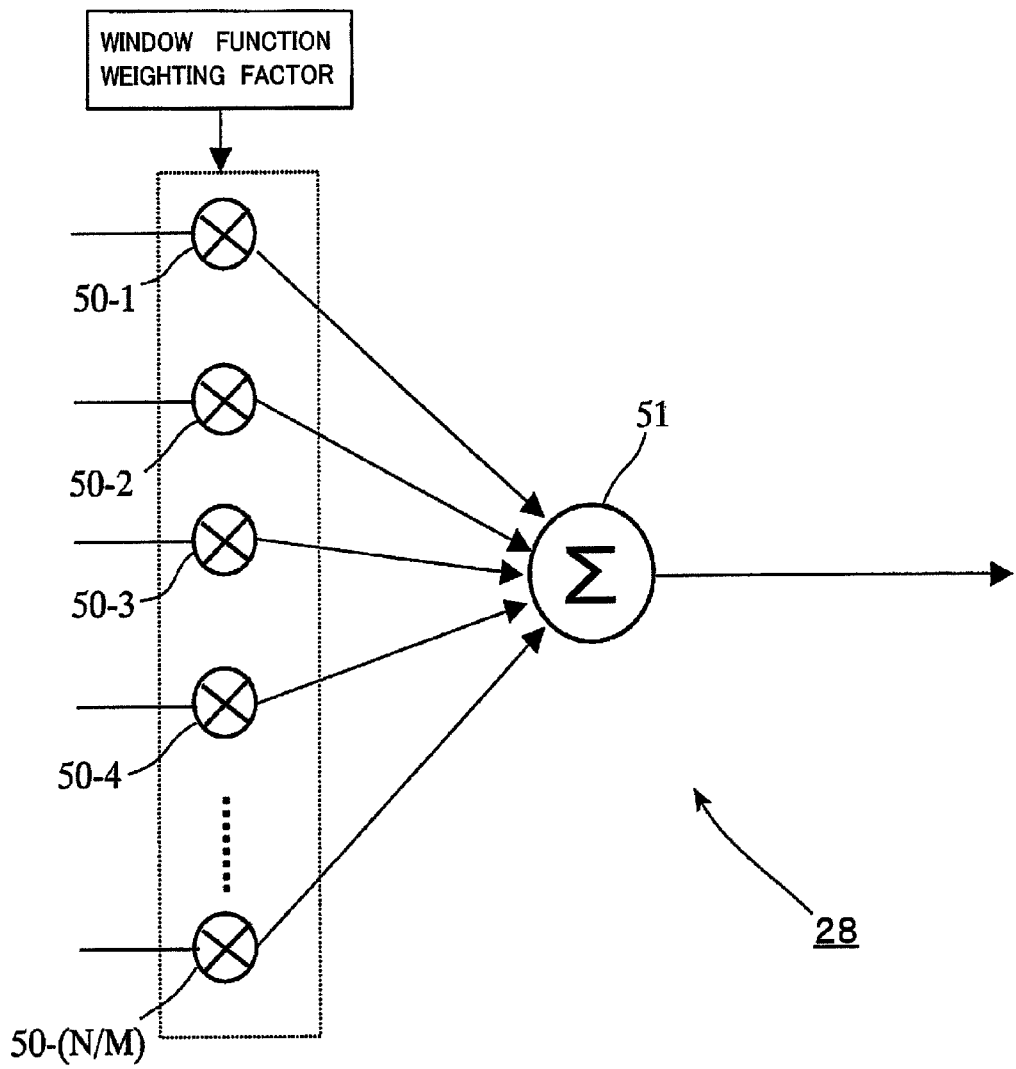
FIG. 8 is a view illustrating a configuration of a calculation circuit according to the fourth embodiment of the present invention.

FIG. 8 is a view illustrating a configuration of the calculation circuit 28. The calculation circuit 28 includes (N/M) multipliers 50-1 to 50-(N/M) and an addition circuit 51. The outputs of the memory selecting switches 27-1 to 27-(N/M) are connected to the multipliers 50-1 to 50-(N/M).

Next, the operations according to the fourth embodiment are described.

The operations of the N A/D converters 1-1 to 1-N are basically the same as those of other embodiments. However, unlike the first to third embodiments, the connection states between the delay adjustment memories 2-1 to 2-N and the calculation circuit 3 are sequentially switched by the memory selecting switches 27-1 to 27-(N/M).

Figure 9:
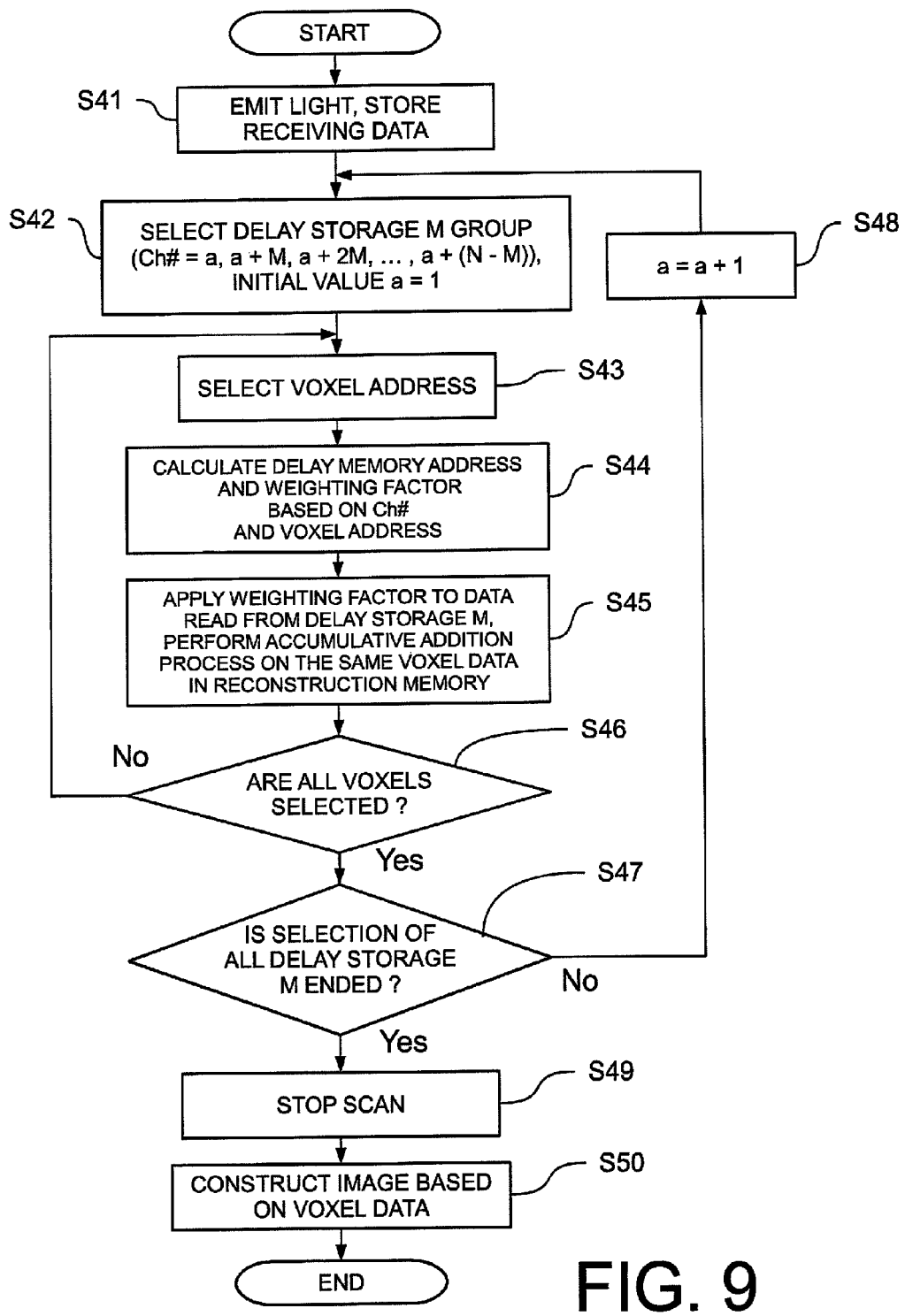
FIG. 9 is a flowchart illustrating operations of the received data processing apparatus of photoacoustic tomography according to the fourth embodiment of the present invention.

FIG. 9 is a flowchart illustrating operations according to the fourth embodiment.

Firstly, the target region of the specimen is irradiated with light, and the acoustic wave generated therefrom is received and digitized by the A/D converters 1-1 to 1-N. The digitized receiving data are stored in the N delay adjustment memories 2-1 to 2-N (refer to step S41). Next, (N/M) delay adjustment memories (a, a+M, a+2M, . . . , a+N-M) that are selected among the N delay adjustment memories 2-1 to 2-N are connected to the multipliers of the calculation circuit 3 (refer to step S42).

Next, the target voxel on which the delay-and-sum processing is performed is determined (refer to step S43), and the delay memory address and the weighting factor required for the delay-and-sum processing are calculated (refer to step S44). Next, the delay-and-sum processing is performed according to the calculated delay memory address and weighting factor, and the result thereof is stored in the reconstruction memory 5 (refer to step S45). Once the delay-and-sum processing on the selected target voxel is ended, the next target voxel is selected, and the delay-and-sum processing is performed (refer to steps S46 and S43). This procedure is repeated until the delay-and-sum processing for all the voxels of the target region is ended. At this time, the delay-and-sum processing for all the voxels of the target region has been done based on the digital data stored in the (N/M) delay adjustment memories (a, a+M, a+2M, . . . , a+N-M) initially selected among the delay adjustment memories 2-1 to 2-N (refer to step S46).

Next, (N/M) delay adjustment memories are newly selected (refer to steps S47 and S48). FIG. 9 illustrates an example where delay adjustment memories (a+1, a+M+1, a+2M+1, . . . , a+N-M+1) are newly selected among the N delay adjustment memories 26-1 to 26-N. After the delay adjustment memories are selected, the delay-and-sum processing is performed on all the voxels of the target region (refer to steps S43 to S46).

The procedure is repeated until all the delay adjustment memories 2-1 to 2-N are selected (refer to step S47). If reading the group of all the delay adjustment memories is ended, the reading is ended (refer to step S49), and the voxel data stored in the reconstruction memory 5 are read to be transmitted to the image construction unit (refer to step S50).

In addition, in this case, although the same target voxel data may be read from different delay adjustment memories 2-1 to 2-N, the memory control circuit 4 and the reconstruction memory 5 perform the accumulative addition process or the addition averaging process on the same target voxel data.

As a result, voxel data for all the voxels in the target region are generated.

In this manner, the memory selecting switches 27-1 to 27-(N/M) are disposed between the delay adjustment memories 2-1 to 2-N and the calculation circuit 28, so that the calculation circuit 28 can be miniaturized.

In the procedure shown in FIG. 9, the delay-and-sum processing is performed on the receiving data obtained from one-time reception by sequentially selecting a plurality of groups divided from the delay adjustment memories 2-1 to 2-N. Therefore, in comparison with, for example, the first embodiment, a long time is taken to generate all the voxel data in the target region. In the case of photoacoustic tomography, because of limitations on the light source, the light irradiation time (as mentioned previously) needs to be set to be a predetermined time or more. Therefore, even when the delay-and-sum processing is performed in a time division manner as in this embodiment, the generation of all the voxel data of the target region can be completed by the time of the next light irradiation. In other words, in the fourth embodiment, the processing does not have the bad influence on frame rate that one might expect from a voluminous amount of processing, and the real-time characteristics of the photoacoustic tomography image processing are not impaired.

In the fourth embodiment, the memory control circuit 4 and the reconstruction memory 5 are also provided in order to process and store the target voxel data, so that all the data in the delay adjustment memories 2-1 to 2-N need not be processed by the calculation circuit 28 simultaneously. Therefore, all the voxel data in the target region can be generated in a time division manner by a miniaturized received data processing apparatus of photoacoustic tomography.

Herein, the selection scheme of the delay adjustment memories 2-1 to 2-N is not necessarily the same as that shown in FIG. 7, but the selection scheme may be suitably determined as needed.

In addition to the configuration illustrated as the fourth embodiment, a switching circuit may be disposed between the A/D converters and the delay adjustment memories, so that the acoustic wave may be received while the connection states between the A/D converters and the delay adjustment memories are sequentially switched (not shown). For example, when the total number of A/D converters is L and the total number of delay adjustment memories is N (L>N), the connection states between the A/D converters and the delay adjustment memories are sequentially switched each reception. In addition, all the A/D converters in which reception is to be performed are selected, so that the processes are continuously performed until the delay-and-sum processing for all the target voxels is ended. Due to the switching circuit disposed between the A/D converters and the delay adjustment memories, the apparatus can be configured with a smaller number of delay adjustment memories than of A/D converters.

In addition to the illustrated configuration, similarly to the second embodiment, as shown in FIG. 4, a switching circuit may be disposed between the acoustic wave detector array and the A/D converters (not shown). In this manner, due to the switching circuit disposed between the acoustic wave detector array and the A/D converters, the apparatus can be configured with a smaller number of A/D converters than of acoustic wave detectors.

Accordingly, the acoustic wave may be received while the connection states between the calculation circuit 28 and the delay adjustment memories, connection states between the A/D converters and the delay adjustment memories, and connection states between the acoustic wave detector array and the A/D converters are sequentially switched.

In addition, the calculation circuit 28 does not necessarily perform only multiplication processing and addition processing, as shown in FIG. 8. If needed, a calculation unit and a signal processing unit required for performing photoacoustic tomography image reconstruction may also be included (not shown). In this case, an independent parameter required for the signal process is calculated for each channel to be applied.

Fifth Embodiment

Figure 10:
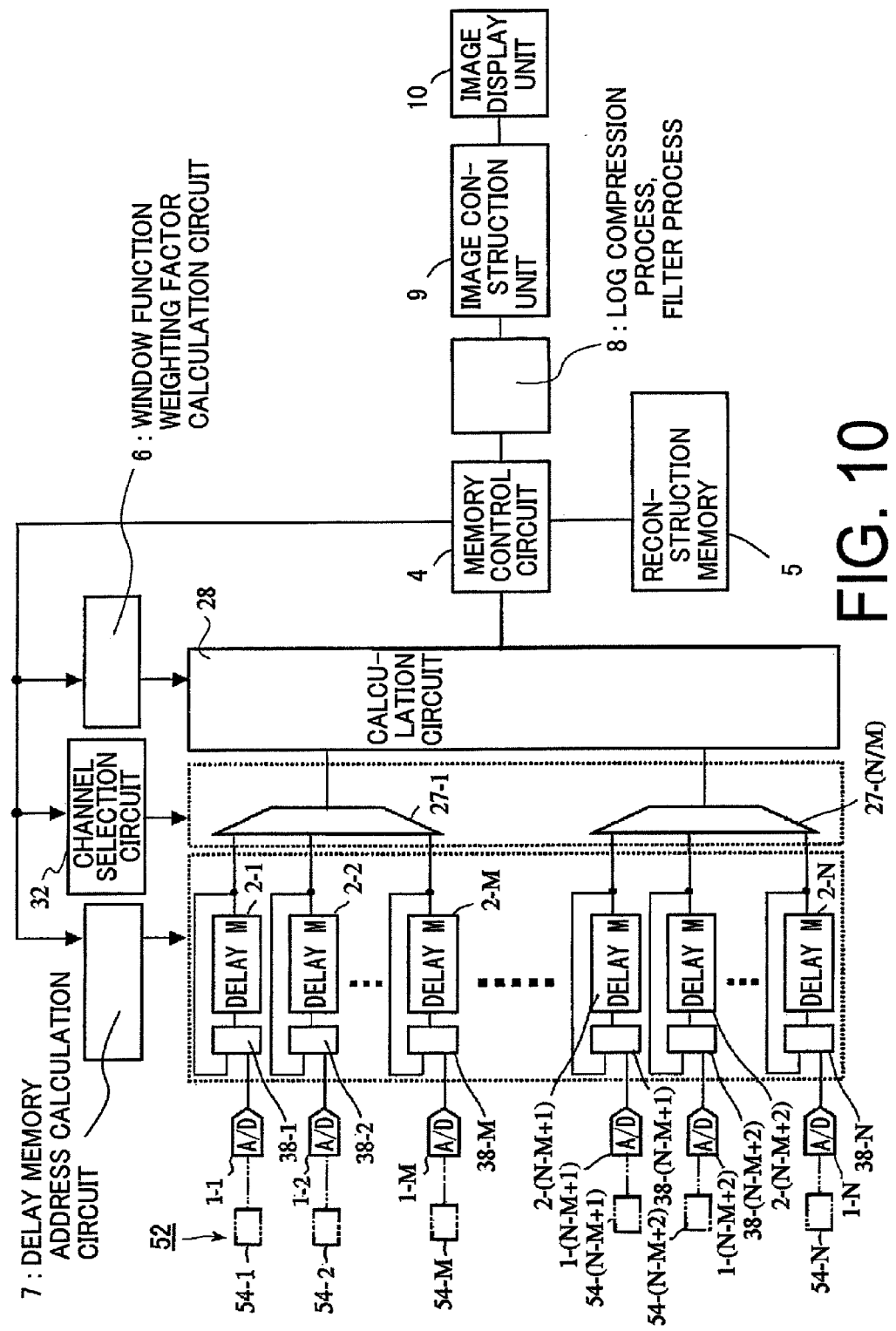
FIG. 10 is a block diagram illustrating a received data processing apparatus of photoacoustic tomography according to a fifth embodiment of the present invention.

FIG. 10 is a view illustrating a received data processing apparatus of photoacoustic tomography according to a fifth embodiment of the present invention. In FIG. 10, the total number of channels of the received data processing apparatus of photoacoustic tomography is N.

The acoustic wave receiving data forming apparatus also includes N A/D converters 1-1 to 1-N, N delay adjustment memories (DELAY M) 2-1 to 2-N, and a calculation circuit 28. In addition, the apparatus further includes a memory control circuit 4, a reconstruction memory 5, a window function weighting factor calculation circuit 6, a delay memory address calculation circuit 7, a signal processing block 8 (log compression processing, filter processing), an image construction unit 9, and an image display unit 10.

In addition, similarly to the fourth embodiment, memory selecting switches 27-1 to 27-(N/M) are disposed between the delay adjustment memories 2-1 to 2-N and the calculation circuit 28. In addition, N/M groups each having M delay adjustment memories are connected to the memory selecting switches 27-1 to 27-(N/M), so that the memory selecting switches 27-1 to 27-(N/M) can be configured to be selected by the channel selection circuit 32.

In addition, in the fifth embodiment, similarly to the third embodiment, the addition averaging circuit 38-1 to 38-N as addition processing units are disposed between the A/D converters 1-1 to 1-N and the delay adjustment memories (DELAY M) 2-1 to 2-N. This feature is different as between the fifth and the fourth embodiments. Similarly to the third embodiment, instead of the addition averaging process, an accumulative addition process may be performed.

Next, the operations according to the fifth embodiment are described.

The operations of the A/D converters 1-1 to 1-N are basically the same as those of the fourth embodiment. However, unlike fourth embodiment, the delay adjustment memories 2-1 to 2-N cooperate with the addition averaging circuits 38-1 to 38-N to perform the addition averaging process on the receiving data.

In photoacoustic tomography, when the S/N ratio of the acoustic wave generated from light irradiation of the specimen is low, there is a need to perform an addition averaging process on the receiving signal. In the fourth embodiment, the addition averaging circuits 38-1 to 38-N cooperate with the delay adjustment memories 2-1 to 2-N to store the addition-averaging-processed receiving data in the delay adjustment memories 2-1 to 2-N, and after that, the delay-and-sum processing is performed on the target voxel data. According to the fifth embodiment, target voxel data having an improved S/N ratio can be obtained.

In the case of photoacoustic tomography, because of limitations on the light source, the light irradiation time needs to be set to be a predetermined time or more. In the present embodiment, the formation of the photoacoustic tomography receiving data is performed using the light irradiation interval, that is, the waiting time. Therefore, after the light irradiation is performed multiple times to perform the addition averaging process, if the generation of all the voxel data in the specimen target region is ended before the next light irradiation starts, the real-time characteristics of the photoacoustic tomography image are maintained without being diminished.

In the present embodiment, the memory control circuit 4 and the reconstruction memory 5 are provided in order to process and store the target voxel data, so that all the data in the delay adjustment memories 2-1 to 2-N need not to be processed by the calculation circuit 28 simultaneously. Therefore, all the voxel data in the target region can be generated in a time division manner by a miniaturized received data processing apparatus of photoacoustic tomography.

Herein, the selection scheme of the delay adjustment memories 2-1 to 2-N is not necessarily the same as that shown in FIG. 10, but may be suitably determined as needed.

In addition to the illustrated configuration of this embodiment, a switching circuit may be disposed between the A/D converters and the addition averaging circuits, so that the acoustic wave may be received while the connection states between the A/D converters and the addition averaging circuits are sequentially switched (not shown). For example, when the total number of A/D converters is L and the total number of addition averaging circuits is N (L>N), the connection states between the A/D converters and the addition averaging circuits are sequentially switched each reception. In addition, all the A/D converters in which reception is to be performed are selected, so that the processes are continuously performed until the delay-and-sum processing for the target voxels is ended. Due to the switching circuit disposed between the A/D converters and the addition averaging circuits, the apparatus can be configured with a smaller number of addition averaging circuit and delay adjustment memories than of A/D converters.

In addition to the illustrated configuration, similarly to the second embodiment, as shown in FIG. 4, a switching circuit may be additionally disposed between the acoustic wave detector array and the A/D converters (not shown). In this manner, due to the switching circuit disposed between the acoustic wave detector array and the A/D converters, the apparatus can be configured with a smaller number of A/D converters than of acoustic wave detectors.

Accordingly, the acoustic wave may be received while the connection states between the calculation circuit 28 and the delay adjustment memories 2-1 to 2-N, the connection states between the A/D converters and the addition averaging circuits, and the connection states between the acoustic wave detector array and the A/D converters are sequentially switched.

In addition, according to the aforementioned embodiments, the operating frequency of a circuit that can change processing speed of the voxel data composition can be improved by changing the operating frequency of the configuration subsequent to (that is, downstream of) the A/D converters. In addition, a plurality of the circuits are disposed in parallel, so that the speed of generating the voxel data can be improved.

In addition, although the above description of the illustrated embodiments is made taking into consideration three-dimensional image reconstruction, pixel data rather than voxel data may be used as the minimum constitution unit, to perform two-dimensional image reconstruction.

While the present invention has been particularly shown and described with reference to embodiments thereof, it will be understood by those skilled in the art that various changes in form and details may be made therein without departing from the spirit and scope of the present invention as defined by the appended claims.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-227091, filed on Sep. 4, 2008, which is hereby incorporated by reference herein in its entirety.

The invention claimed is:

1. A received data processing apparatus, comprising:
   a plurality of conversion units that each perform digitization to digitize signals output from a plurality of acoustic wave detectors that receive acoustic waves generated in a specimen by absorption of light;
   a plurality of first storage units each of which stores digital signals output from a respective one of said plurality of conversion units, only one of said first storage units receiving and storing digital signals from a given one of said conversion units;
   a data composition unit that reads digital signals derived from the acoustic waves that originated from a target position in the specimen from said plurality of first storage units, reading from each of said first storage units the digital signal stored therein from said respective one of said conversion units, and adds digital signals read from said plurality of first storage units to compose data of the target position, and
   an image construction unit that constructs an image based on the composed data of the target position,
   wherein each of said plurality of first storage units stores at least the digital signals derived from acoustic waves generated by a single pulse of light, and
   wherein said data composition unit composes photoacoustic tomography data of a plurality of target positions distributed in a three-dimensional region of the specimen by repetitively, for each pixel or voxel, reading digital signals for the single pulse of light stored in each of said plurality of first storage units, based on travel times that are required for acoustic waves from each of the plurality of target positions to reach the detectors.

2. The received data processing apparatus according to claim 1, wherein said plurality of first storage units store digital signals sequentially for each channel of plural channels that transmits a digital signal derived from the received acoustic waves.

3. The received data processing apparatus according to claim 1, further comprising:
   a second storage unit that stores the data of the plurality of target positions in the specimen output from said data composition unit.

4. The received data processing apparatus according to claim 3, further comprising
   a control unit that reads the data of the target position from said second storage unit and transmits the data of the target position to said image construction unit,
   wherein said image construction unit constructs the image based on the data of the plurality of target positions stored in said second storage unit.

5. The received data processing apparatus according to claim 3,
   further comprising a switching unit for connecting said plurality of first storage units and said data composition unit,
   wherein said switching unit switches which one of said plurality of first storage units is connected to said data composition unit.

6. The received data processing apparatus according to claim 5, wherein said second storage unit comprises an addition unit that adds the data of the target positions which correspond to an identical target position and stores the added data.

7. The received data processing apparatus according to claim 1, wherein said data composition unit completes composition of the data of the plurality of target positions in a target region within the light-irradiation interval.

8. The received data processing apparatus according to claim 1, further comprising:
   the plurality of acoustic wave detectors; and
   a connection switch unit that switches at least one connection state from among connection states between said plurality of first storage units and said data composition unit, connection states between said plurality of conversion units and said plurality of first storage units, and connection states between said plurality of acoustic wave detectors and said plurality of conversion units.

9. The received data processing apparatus according to claim 1, wherein said second storage unit comprises an addition unit that adds the data of the target positions which correspond to an identical target position and stores the added data.

10. The received data processing apparatus according to claim 1, further comprising:
    an address calculation unit that calculates delay times based on the travel times that are required for the acoustic wave from the target position to reach said acoustic wave detectors and supplies addresses where the digital signals derived from acoustic waves that originated from the target position are to be stored, corresponding to the delay times, to said plurality of first storage units.

11. The received data processing apparatus according to claim 1, further comprising:
a weighting factor calculation unit that calculates weight factors on respective channels which transmit the digital signals and applies the calculated weighting factors to said data composition unit.

12. The received data processing apparatus according to claim 1, further comprising:
a controller that changes a composition processing speed of the data of the target position by changing an operating frequency of a configuration subsequent to said conversion units.

13. The received data processing apparatus according to claim 1, wherein a plurality of said configurations subsequent to said conversion units are disposed in parallel.

14. The received data processing apparatus according to claim 1,
wherein said data composition unit composes photoacoustic tomography data of a plurality of target positions distributed in the three-dimensional region of the specimen by repetitively reading the digital signals for the single pulse of light stored in each of said plurality of first storage units, n times (where n is a natural number greater than 1), each time reading the digital signals stored in said first storage units, based on travel times that are required for acoustic waves from each of the plurality of target positions to reach said detectors, to compose data of a respective target position.

15. A photoacoustic apparatus, comprising:
a light source;
a plurality of acoustic wave detectors that convert acoustic waves generated in a specimen by absorption of light from said light source into received analog signals;
a plurality of conversion units, each converting one of the received analog signals into a received digital signal;
a plurality of first storage units that store the received digital signals output from said plurality of conversion units in time sequence; and
a data composition unit that reads the received digital signals, that originated from a target position from among a plurality of target positions in a target region of the specimen, from each of said plurality of first storage units based on travel times that are required for acoustic waves from the target positions to reach said plurality of acoustic detectors, and composes target position data which is data of the acoustic waves on each of the plurality of target positions; and
a second storage unit that stores the target position data of each of the plurality of target positions in the target region output from said data composition unit,
wherein each of said plurality of first storage units stores the received digital signals derived from the acoustic waves generated by a single pulse of light from said light source,
wherein said data composition unit composes the target position data of the plurality of the target positions in the target region by repetitively reading the received digital signals that are stored in said plurality of first storage units and are derived from the single pulse of light, and
wherein said second storage unit stores data calculated by adding a plurality of target position data which correspond to a same target position, the plurality of target position data being derived from acoustic waves received in different reception regions.

16. The photoacoustic apparatus according to claim 15, wherein said plurality of first storage units store digital signals sequentially for each channel of plural channels that transmits a digital signal derived from the received acoustic waves.

17. The photoacoustic apparatus according to claim 16, further comprising:
a weighting factor calculation unit that calculates weight factors on respective channels which transmit the digital signals and applies the calculated weighting factors to said data composition unit.

18. The photoacoustic apparatus according to claim 15, further comprising:
an image construction unit that constructs an image based on the data of the plurality of target positions stored in said second storage unit; and
a control unit that reads the data of the target position from said second storage unit and transmits the data of the target position to said image construction unit.

19. The photoacoustic apparatus according to claim 15, wherein said data composition unit composes the data of the plurality of target positions in the target region within a light-irradiation interval of said light source.

20. The photoacoustic apparatus according to claim 15,
further comprising a switching unit for connecting said plurality of first storage units and said data composition unit,
wherein said switching unit switches which one of said plurality of first storage units is connected to said data composition unit.

21. A data processing apparatus for processing data acquired by a plurality of acoustic wave detectors, the apparatus comprising:
a plurality of A/D converters each configured to digitize a signal output from a respective one of a plurality of acoustic wave detectors that receive an acoustic wave generated from a specimen by irradiation with a pulse of light at an irradiation time, a target region of the specimen being divided into a plurality of voxels arranged in three dimensions and delay times, taken from each voxel to the plurality of acoustic wave detectors, being calculated;
a plurality of storage units each configured to store the digitized signal acquired from a respective one of said plurality of A/D converters, a plurality of digitized signals, digitized by the plurality of A/D converters and corresponding to the acoustic wave generated from the specimen by irradiation with the pulse of light at the irradiation time, being stored by said plurality of storage units;
a data composition unit configured to compose voxel data of each voxel by reading the plurality of digitized signals, stored by said plurality of the storage units, to be summed based on the delay times, the stored digitized signals being repetitively read for composing a plurality of voxel data corresponding to the plurality of voxels arranged in three dimensions; and
an image construction unit that constructs an image based on the plurality of voxel data of the target region.

22. The data processing apparatus according to claim 21, wherein the target region of the specimen is divided into the plurality of voxels arranged in three dimensions.

23. The data processing apparatus according to claim 21, wherein said data composition unit is configured to compose each voxel data of the voxels by using window function weighting factors.

24. The data processing apparatus according to claim 21, wherein said data composition unit is configured to complete composing all voxel data of the plurality of voxels before a next irradiation time after the irradiation time.

25. The data processing apparatus according to claim 21, wherein said data composition unit is configured to compose the entire voxel data of the plurality of voxels, corresponding to the acoustic wave generated from the specimen by irradiation with the pulse of light at the irradiation time, arranged in three dimensions.

26. The data processing apparatus according to claim 21, wherein said data composition unit is configured to compose each voxel data of the plurality of voxels by using other digitized signals corresponding to another acoustic wave generated from the specimen by irradiation with a pulse of light at another irradiation time.

* * * * *